United States Patent [19]

Kempe

[11] Patent Number: 4,697,002
[45] Date of Patent: Sep. 29, 1987

[54] CALCITONIN GENE RELATED PEPTIDE ANALOGS WITH AMINO ACID SUBDSTITUENTS AT THE PENULTIMATE POSITION 36

[76] Inventor: Tomas G. Kempe, 16604 Windermere Pl., Minnetonka, Minn. 55345

[21] Appl. No.: 812,900

[22] Filed: Dec. 23, 1985

[51] Int. Cl.$^4$ .............................................. C07K 7/10
[52] U.S. Cl. .................................................... 530/324
[58] Field of Search ................... 530/307, 324; 514/11

[56] References Cited

U.S. PATENT DOCUMENTS

| | | | |
|---|---|---|---|
| 3,929,758 | 12/1975 | Hughes et al. | 530/307 |
| 4,530,838 | 7/1985 | Evans et al. | 514/11 |
| 4,549,986 | 10/1985 | Evans et al. | 530/324 |

*Primary Examiner*—Delbert R. Phillips
*Attorney, Agent, or Firm*—James R. Haller; Mary P. Bauman

[57] ABSTRACT

New calcitonin gene related peptide analogs (CGRP) are disclosed which have biological activity of the same type as known calcitonin gene related peptides and which have an amino acid substituent at position 36 or the penultimate position instead of the naturally occurring amino acid—Ala.

5 Claims, No Drawings

CALCITONIN GENE RELATED PEPTIDE ANALOGS WITH AMINO ACID SUBDSTITUENTS AT THE PENULTIMATE POSITION 36

FIELD OF THE INVENTION

This invention relates to calcitonin gene related peptide analogs (CGRP) having biological activity and to peptides which can be converted to biologically active CGRP analogs.

BACKGROUND OF THE INVENTION

All known calcitonin gene related peptide ("CGRP") analogs share some common structural features. Each is 37 amino acids long with a C-terminal phenylalanine amide and an N-terminal disulfide linked ring from position 2 through position 7. One of the human CGRP's, for example, has the following formula (Morris, H. R. et al. (1984) Nature 308, 746–748)

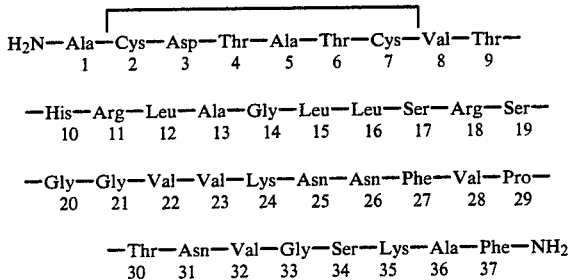

A second recently characterized human CGRP differs from the above by having the amino acid Asn at position 3, Met at position 22 and Ser at position 25 (Steenbergh, P. H. et al. (1985) Febs Lett. 183, 403–407). There are also two known CGRP of rat origin. The first to be characterized differs from the human sequence above by having Ser at position 1, Asn at position 3, Asp at position 25 and Glu at position 35 (Amara, S. G. et al. (1982) Nature 298, 240–244) A recently characterized second rat CGRP differs from the human structure by having Ser at position 1, Asn at position 3, and Asp at position 25 (Amara, S. G. et al. (1985) Science 229, 1094-97)

It has been shown that CGRP and calcitonin are derived from the same gene. The calcitonin gene is alternatively expressed in a tissue specific fashion producing either the calcium-regulating hormone calcitonin in the thyroid or the neuropeptide CGRP in the brain (Rosenfeld, M. G. et al. (1983) Nature 304, 129–135). Recently, it has been shown that both peptides are produced in thyroid parafollicular cells (Lee, Y. et al. (1985) Neuroscience 15, 1227–1237; Self, C. H. et al. (1985) Peptides 6, 627–630) which indicate a peripheral physiological role. Both calcitonin and CGRP interact with the same receptor in some experimental conditions, thus showing that both peptides share some common structural features (Goltzman, D. and Mitchell, J. (1985) Science 227, 1343–1345; Wohlwend, A. et al. (1985) Biochem. Biophys. Res. Commun. 131, 537–542). The inhibition of gastric acid secretion by both peptides also confirms such similarities (Hughes, J. J. et al, (1984) Peptides 5, 665–667; Stevenson, J. C. (1985) Clin. Endrocrinol. 22, 655–660; Lenz. H. J. (1985) Gut 26, 550–555). CGRPs are potent vasodilators; a property that has not been detected in human calcitonin (Brain, S. D. et al. (1985) Nature 313, 54–56).

U.S. Pat. No. 4,530,838 discloses two naturally occurring rat CGRPs and U.S. Pat. No. 4,549,986 discloses human CGRP.

SUMMARY OF THE INVENTION

I have discovered that amino acid substituents at position 36 in CGRP have biological activity of the same type as naturally occurring CGRP and calcitonin analogs. A significant difference in structure is that in these new peptides, the amino acid sequence does not contain Ala at position 36 of the known CGRP sequence. The new peptides have good potency and quality when compared with known CGRP analogs. The introduction of such substituents may result in increased bioactivity due to specific structural features of the peptide at the receptor site. I suggest that some of the similarities in biological activities between calcitonins and CGRPs are partly due to the sequence homology at the C-terminal portion of the peptides as shown below:

Salmon 1 calcitonin C-terminal sequence (amino acids 25-32)
—Thr—Asn—Thr—Gly—Ser—Gly—Thr—Pro—$NH_2$
25    26    27    28    29    30    31    32

Human CGRP C-terminal sequence (Amino acids 30-37)
—Thr—Asn—Val—Gly—Ser—Lys—Ala—Phe—$NH_2$
30    31    32    33    34    35    36    37

The CGRP analogs may be those of human or rat origin.

Preferred amino acid substituents are Val, Leu, Ile, Ser, Hse, Thr, Asp, Asn, Glu and Gln. A preferred analog is substituted human CGRP of the formula:

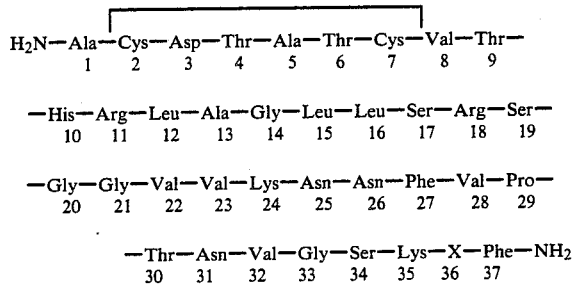

in which X is Val, Leu, Ile, Ser, Hse, Thr, Asp, Asn, Glu or Gln. Particularly preferred peptides of the invention are the human analogs, especially [Val$^{36}$]CGRP, [Ser$^{36}$]CGRP, [Hse$^{36}$]CGRP, [Thr$^{36}$]CGRP, [Glu$^{36}$]CGRP, [Gln$^{36}$]CGRP, [Asp$^{36}$]CGRP and [Asn$^{36}$]CGRP.

DESCRIPTION OF THE INVENTION

Resin Peptide Synthesis

The synthesis of CGRP analogs may follow the stepwise solid phase strategy reported in Merrifield, R. B. (1963) J. Am. Chem. Soc. 85, 2149–2154, the teachings of which are incorporated herein by reference. The acid labile tert-butyloxycarbonyl (Boc-) group may be used for temporary alpha-N protection and the more acid stable groups may be used for protection of the side chains of the amino acids. Amino acid derivatives are listed in Table 1 and abbreviations are listed in Table 2. Attachment of the peptide chain to a copolymer matrix of styrene and 1% divinylbenzene may employ a benzhydrylamine type "handle" as reported in Pietta, P. G. et al. (1970) Chem. Commun. 650-651; Hruby, V. J. et al. (1977) J. Org. Chem. 42, 3552-3556; and Tam, J. P. et al. (1981) Tetrahedron Lett. 22, 2851-2854, which teachings also are incorporated by reference. All amino acids may be incorporated following a double coupling protocol with some modifications for particular amino acids. For all reactions, except for arginine and asparagine, the first coupling employs the preformed symmetric anhydride method (Hagenmaier, H. and Frank, H. (1972) Hoppe-Seyler's Z. Physiol. Chem. 353, 1973-1976) in dichloromethane and the second coupling employs the preformed hydroxybenztriazole ester method (König, W. and Geiger, R. (1970) Chem. Ber. 103, 788-798) in dimethyl formamide (DMF). For Boc-Arg(Tos), standard DCC coupling conditions are employed to reduce the risk of lactam formation. The second coupling is done with the active HOBt ester method in DMF. Boc-Asn is exclusively coupled as HOBt esters in DMF to reduce nitrile and amidine formation (Mojsov, S. et al. (1980) J. Org. Chem. 45, 555-560). N-epsilon-(2-Chlorobenzyloxycarbonyl)lysine, Lys(ClZ), is used because it is more stable than the benzyloxycarbonyl derivative to the acid deprotection steps and it also avoids side chain branching (Erickson, B. W. and Merrifield, R. B. (1972) J. Am. Chem. Soc. 95, 3757-3763). The beta-cyclohexyl ester (cHex) of Boc-Asp-OH is used; it is also more stable to acids and thus minimizes aspartimide formation (Tam, J. P. (1979) Tetrahedron Lett. 4033-4036). The quantitative ninhydrin reaction is routinely used throughout the synthesis to monitor the extent of coupling after each cycle (Sarin, V. K. et al. (1981) Anal. Biochem. 117, 147-157).

TABLE 1

Amino acid derivatives for synthesis of CGRP analogs at position 36. [$Ser^{36}$] human CGRP

| cycl nr. and amino acid | protected amino acids | MW | mmol | g | coupling procedure |
|---|---|---|---|---|---|
| 37 | Phe—benzhydryl amine resin | | 1 | 2 | A |
| 36, 34, 19, 17 | Boc—Ser(Bzl) | 295.1 | 8 | 2.36 | A |
| | | | 4 | 1.18 | |
| 35, 24 | Boc—Lys(Cl—Z) | 314.8 | 8 | 2.50 | A |
| | | | 4 | 1.25 | |
| 33, 21, 20, 14 | Boc—Gly | 175.2 | 8 | 1.40 | A |
| | | | 4 | 0.70 | |
| 32, 28, 23, 22, 8 | Boc—Val | 217.1 | 8 | 1.74 | A |
| | | | 4 | 0.87 | |
| 31, 26, 25 | Boc—Asn | 232.2 | 4 | 0.93 | B |
| 30, 9, 6, 4 | Boc—Thr(Bzl) | 309.1 | 8 | 2.48 | A |
| | | | 4 | 1.24 | |
| 29 | Boc—Pro | 215.1 | 8 | 1.72 | A |
| | | | 4 | 0.86 | |
| 27 | Boc—Phe | 265.2 | 8 | 2.12 | A |
| | | | 4 | 1.06 | |
| 18, 11 | Boc—Arg(Tos) | 442.5 | 4 | 1.77 | C |
| 16, 15, 12 | Boc—Leu | 249.2 | 8 | 2.0 | A |
| | | | 4 | 1.0 | |
| 13, 5, 1 | Boc—Ala | 189.2 | 8 | 1.51 | A |
| | | | 4 | 0.76 | |
| 10 | Boc—His(Tos) | 409.2 | 8 | 3.28 | A |
| | | | 4 | 1.64 | |
| 7, 2 | Boc—Cys(4-Me—Bzl) | 325.2 | 8 | 2.60 | A |
| | | | 4 | 1.40 | |
| 3 | Boc—Asp(OcHex) | 328.4 | 8 | 2.63 | A |
| | | | 4 | 1.31 | |

TABLE 2

Abbreviations (Biochem Biophys. Acta 133, 1-5 (1967)).

Boc = tert-butyloxycarbonyl
Bzl = benzyl
Tos = tosyl

TABLE 2-continued

Abbreviations (Biochem Biophys. Acta 133, 1-5 (1967)).

$Cl_2Bzl$ = 2,6-dichlorobenzyl
Cl—Z = o-chlorobenzyloxycarbonyl
OcHex = gamma-cyclohexyl ester
4-Me—Bzl = 4-methylbenzyl
HOBt = N—hydroxybenztriazole
DIEA = diisopropylethylamine
DCC = dicyclohexylcarbodiimide
DMF = N,N—dimethylformamide
CM = carboxymethyl
TFA = trifluoroacetic acid
HPLC = high performance liquid chromatography
Ala = L-alanyl
Pro = L-prolyl
Ser = L-seryl
Hse = L-homoseryl
Gly = glycyl
Thr = L-threonyl
Asn = L-asparaginyl
Arg = L-arginyl
Tyr = L-thyronyl
Phe = L-phenylalanyl
Leu = L-leucyl
Lys = L-lysyl
His = L-histidyl
Asp = L-asparagyl
Val = L-valyl
Cys = L-cysteinyl
Glu = L-glutamyl
Gln = L-glutaminyl
Met = L-methionyl
Ile = L-isoleucyl Resin Peptide Cleavage and Purification Cleavage of the peptides from the resin and removal of all the remaining protecting groups is accomplished by treatment with anhydrous hydrogen fluoride in the presence of anisole (Yamashiro, D. and Li, C. H. (1978) J. Am. Chem. Soc. 100, 5174-5179). Crude peptide is removed from the resin by washing with 10% aqueous acetic acid. After lyophilization, the residue may be treated with dithiothreitol (Cleland, W. W. (1964) Biochemistry 3, 480–482) in sodium phosphate buffer at pH 7.5. The intramolecular disulfide bond in CGRP between cysteine residues 2 and 7 can be formed by diluting the solution several-fold and adding potassiumferricyanide in aqueous solution. The resultant peptide solution is then concentrated by passing it through a CM-Sephadex, C-25 column and then eluting with a linear gradient of sodium chloride from zero to 0.3 molar in the same phosphate buffer (Live, D. H. et al. (1977) J. Org. Chem. 42, 3556–3561; Moe, G. R. and Kaiser, E. T. (1985) Biochemistry 24, 1971–1976). The sample is finally desalted by gel filtration, concentrated and isolated by HPLC.

While the amino acid substitution at position 36 may be made in human CGRP and rat CGRP, for exemplification, the following detailed disclosure is directed to human CGRP. The formula for our new substitution analogs at position 36 of human CGRP may be written as follows:

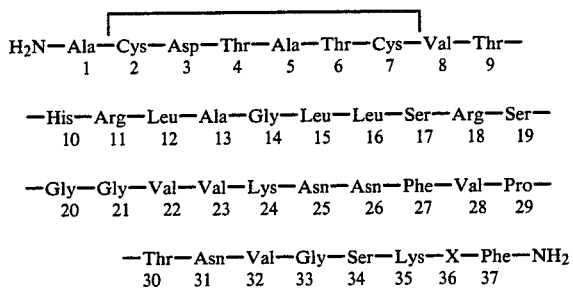

in which X is Ala, Val, Leu, Ile, Hse, Ser, Thr, Asp, Asn, Glu or Gln.

As may be seen from the formula above, 37 amino acids are involved and in this formula, the positions are numbered according to the accepted procedure beginning at position 1 for the Ala on one end of the chain and ending with Phe at position 37 at the other end of the chain. For clarity of description, this same numbering system will be followed in referring to the cycles of the synthesis. The assemmbly of the amino acids begins with cycle 36 which involves the coupling of the amino acid to the Phe moiety, followed by residue 35 and so on to the last amino acid. Protected amino acid derivatives that may be used in the synthesis of CGRP analogs are given in Table 1. The resin which is functionalized with Phe is available from chemical supply houses.

As indicated earlier, three types of coupling procedures are used, depending on the properties of reactants. In Table 1, the amino acid position and cycle number, type of coupling procedure, molecular weights and amount of reactants for the cycle are given. The details for each coupling protocol A, B and C are described below.

RESIN PEPTIDE SYNTHESIS

EXAMPLE 1

[Ser$^{36}$]CGRP: Double coupling protocol using symmetric anhydride and active ester methods may be used to ensure as complete coupling as possible. The following protocol may be used for all amino acids except for arginine and asparagine. The protocol is given for 2 g benzhydryl type resin functionalized with a total of 1 mMol of Phe.

Coupling Procedure A

1. The resin is washed with dichloromethane, $CH_2CH_2$ (30 mL, 6×1 min).
2. Removal of the Boc protecting group is done with 50% TFA in $CH_2Cl_2$ (30 mL, 3×1 min) and with 30 mL for 20 min.
3. The reagent is then removed with $CH_2Cl_2$ wash (30 mL, 6×1 min).
4. Traces of acid are finally removed with 5% DIEA in $CH_2Cl_2$ (30 mL, 2×2 min).
5. A final wash is done before the coupling is completed, $CH_2Cl_2$ (30 mL, 6×1 min).
6. 5 mg of the resin are removed for ninhydrin test.
7. The protected amino acid (listed in Table 1, 8 mMol) dissolved in 10 mL of $CH_2Cl_2$ is treated with DCC (4 mMol, 825 mg) in 3 mL of $CH_2Cl_2$. After 10 min, the solution is filtered and added to the resin. The precipitate is washed with 10 mL of $CH_2Cl_2$ and added to the reaction vessel which is then shaken for 2 h at room temperature.
8. The resin is washed with $CH_2Cl_2$ (30 mL, 4×2 min).
9. The resin is washed with 5% DIEA in $CH_2Cl_2$ (30 mL, 2 min).
10. The resin is washed with $CH_2Cl_2$ (30 mL, 4×2 min).
11. Ninhydrin test is performed.
12. The resin is washed with DMF (30 mL, 2×2 min).
13. HOBt (4 mMol, 540 mg) in 7 mL of DMF at 0° C. is mixed with DCC (4 mMol, 825 mg) in 3 mL $CH_2Cl_2$. The protected amino acid (listed in Table 1, 4 mMol) dissolved in 6 mL of DMF is then added. The mixture is kept for 10 min at 0° C. and is then added to the resin. The mixture is shaken for 2 h at room temperature.
14. The resin is then washed with DMF (30 mL, 2×2 min).
15. The resin is washed with $CH_2Cl_2$ (30 mL, 4×1 min).
16. The resin is washed with 5% DIEA in $CH_2Cl_2$ (30 mL, 2 min).
17. The resin is washed with $CH_2Cl_2$ (30 mL, 3×1 min).
18. Ninhydrin test is performed.

Coupling Procedure B. (Used for the amino acids asparagine):
Steps 1–6 were the same as coupling procedure A.
7. The resin is washed with DMF in $CH_2Cl_2$ (1:2 v/v, 30 mL, 2×2 min).
8. To HOBt (4 mMol, 540 mg) in 7 mL DMF/$CH_2Cl_2$ (1:1 v/v) at 0° C. is added DCC (4 mMol, 825 mg) in 3 mL of $CH_2Cl_2$. To that mixture is then added the protected amino acid (listed in Table 1, 4 mMol) in 6 mL of DMF/$CH_2Cl_2$. The reaction mixture is added to the resin after 10 min at 0° C. The resin is then shaken for 2 h at room temperature.
9. The resin is washed with DMF/$CH_2Cl_2$ (1:2 v/v, 30 mL, 2×2 min).

The steps 8–18 described in coupling procedure A are than followed.

Coupling Procedure C. (Used for the amino acid arginine):
Steps 1–6 are the same as coupling procedure A.
7. The protected amino acid (listed in Table 1, 4 mMol) in 10 mL $CH_2Cl_2$ is added to the resin. DCC (4 mMol, 825 mg) in 3 mL $CH_2Cl_2$ is added after 5 min to the resin. The reaction mixture is then shaken for 2 h at room temperature.

The steps 8-18 described in coupling procedure A are then followed.

EXAMPLE 2

[Thr$^{36}$]CGRP: Boc-Thr(Bzl) is used in cylce 36, and coupling procedure A is employed. The preceding couplings were the same as previously described (Table 1).

EXAMPLE 3

[Asn$^{36}$]CGRP: Boc-Asn is used in cycle 36, and coupling procedure B is employed. The preceding couplings were the same as previously described (Table 1).

In each example, the addition of Ala$^1$ represents the completion of the solid phase synthesis. The Boc group is finally removed by steps 1-6 in coupling procedure A. The resin peptides are then removed from the reaction vessel and dried in vacuum. Cleavage and purification steps are carried out as follows:

RESIN-PEPTIDE CLEAVAGE

The dried resin peptide (2 g) and 2 mL of anisole are placed in a teflon reaction vessel which is cooled in a dry ice-acetone bath and about 15 mL of hydrogen fluoride gas is condensed into the vessel. The mixture is stirred at 0° C. in an ice bath for 45 min. The hydrogen fluoride is then evaporated under vacuum, using first a water aspirator and later a high vacuum pump. The residue is triturated with 5×30 mL of ethyl acetate, and the peptide was extracted from the resin beads with 100 mL of 10% aqueous acetic acid solution. The mixture was lyophilized to dryness.

PURIFICATION OF CRUDE PEPTIDES

A 100 mg sample of the lyophilized peptide is treated with excess dithiothreitol (5 mMol) in 5 mL of 50 mM sodium phosphate buffer at pH 7.5 for 1 h at room temperature. The intramolecular disulfide bond between cysteine residues 2 and 7 is formed by diluting the peptide solution to a volume of 1 liter in the same buffer. A solution of 20 mM K$_3$Fe(CN)$_6$ is slowly added with stirring until a persistant yellow color is obtained. The resultant dilute peptide solution is concentrated by passing it through a CM-Spehadex, C-25 column and then eluting with a linear gradient of NaCl from zero to 0.3M employing the same buffer. Fractions from this column may be desalted on a Sephadex G-15 column, eluting with a 0.03M aqueous acetic acid solution. Samples for biological testing are isolated on an analytical HPLC (column: Altex ODS, 5 micron, 4.6×250 mm, flow 1.5 mL/min, gradient of 30-45% acetonitrile in 0.1M ammonium acetate buffer at pH 5.5).

The HPLC isolated samples are hydrolyzed with 5.5M hydrochloric acid, and amino acid analyses are performed to confirm the chemical composition. The new polypeptides are biologically active. They exhibit similarities to both calcitonins and CGRPs in lowering gastric acid secretion.

While only certain embodiments of my invention have been described in specific details, it will be apparent to those skilled in the art that many other specific embodiments may be practiced and many changes may be made, all within the spirit of the invention and the scope of the appended claims.

What is claimed is:

1. [Ser$^{36}$] human calcitonin gene-related peptide.
2. [Hse$^{36}$] human calcitonin gene-related peptide.
3. [Thr$^{\mp}$] human calcitonin gene-related peptide.
4. [Asp$^{36}$] human calcitonin gene-related peptide.
5. [Asn$^{36}$] human calcitonin gene-related peptide.

* * * * *